United States Patent
Pei

(10) Patent No.: US 8,439,818 B2
(45) Date of Patent: May 14, 2013

(54) SLEEP INDUCING APPARATUS AND ELECTRONIC DEVICE USING THE SAME

(75) Inventor: Guang-Yu Pei, Shenzhen (CN)

(73) Assignees: Hong Fu Jin Precision Industry (ShenZhen) Co., Ltd., Shenzhen (CN); Hon Hai Precision Industry Co., Ltd., New Taipei (TW)

(*) Notice: Subject to any disclaimer, the term of this patent is extended or adjusted under 35 U.S.C. 154(b) by 1006 days.

(21) Appl. No.: 12/468,043

(22) Filed: May 18, 2009

(65) Prior Publication Data
US 2009/0287039 A1    Nov. 19, 2009

(30) Foreign Application Priority Data
May 19, 2008 (CN) .......................... 2008 1 0301628

(51) Int. Cl.
*A61M 21/00* (2006.01)
(52) U.S. Cl.
USPC .......................................................... 600/28
(58) Field of Classification Search ............ 600/26–28, 600/545
See application file for complete search history.

(56) References Cited

U.S. PATENT DOCUMENTS

| | | | |
|---|---|---|---|
| 5,241,967 A * | 9/1993 | Yasushi et al. | 600/545 |
| 7,155,285 B2 | 12/2006 | Wang et al. | |
| 2006/0106276 A1 * | 5/2006 | Shealy et al. | 600/27 |

FOREIGN PATENT DOCUMENTS

| CN | 2520878 Y | 11/2002 |
|---|---|---|
| CN | 1806861 A | 7/2006 |

OTHER PUBLICATIONS

Kang-Shoo He, The Application of the Changing Resistance Character of the Field Effect Transistor, Journal of Yiyang Teachers College, Oct. 31, 1988, Abstract, 1988-1th, Hunan City University, CN.

* cited by examiner

*Primary Examiner* — Christine Matthews
(74) *Attorney, Agent, or Firm* — Altis Law Group, Inc.

(57) ABSTRACT

An apparatus for inducing sleep includes an audio generator, a signal generator, and a signal processor. The audio generator generates audio signals. The signal generator generates electrical signals with a frequency between 0.4 HZ to 4 HZ. The signal processor adjusts amplitudes of the audio signals according to the frequency, and outputs the adjusted audio signals.

10 Claims, 3 Drawing Sheets

SLEEP INDUCING APPARATUS AND ELECTRONIC DEVICE USING THE SAME

BACKGROUND

1. Technical Field

The present disclosure generally relates to electronic technology, and particularly to a sleep inducing apparatus and an electronic device using the same.

2. Description of Related Art

Sleep is important part of a person's well being. Sleep deprivation often leads to tiredness and irritability.

Nowadays, under job stress and other stressful daily activities, many people experience insomnia. Thus, they depend on drugs to fall asleep. However, this may cause drug dependence after long term usage of the drugs.

Therefore, a non-drug sleep inducing apparatus is desired, and an electronic device using the apparatus is also desired.

Other advantages and novel features will become more apparent from the following detailed description of exemplary embodiments when taken in conjunction with the accompanying drawings.

DETAILED DESCRIPTION

References will now be made to the drawings to describe exemplary embodiments of a sleep inducing apparatus and an electronic device using the apparatus for inducing sleep.

Figure 1:
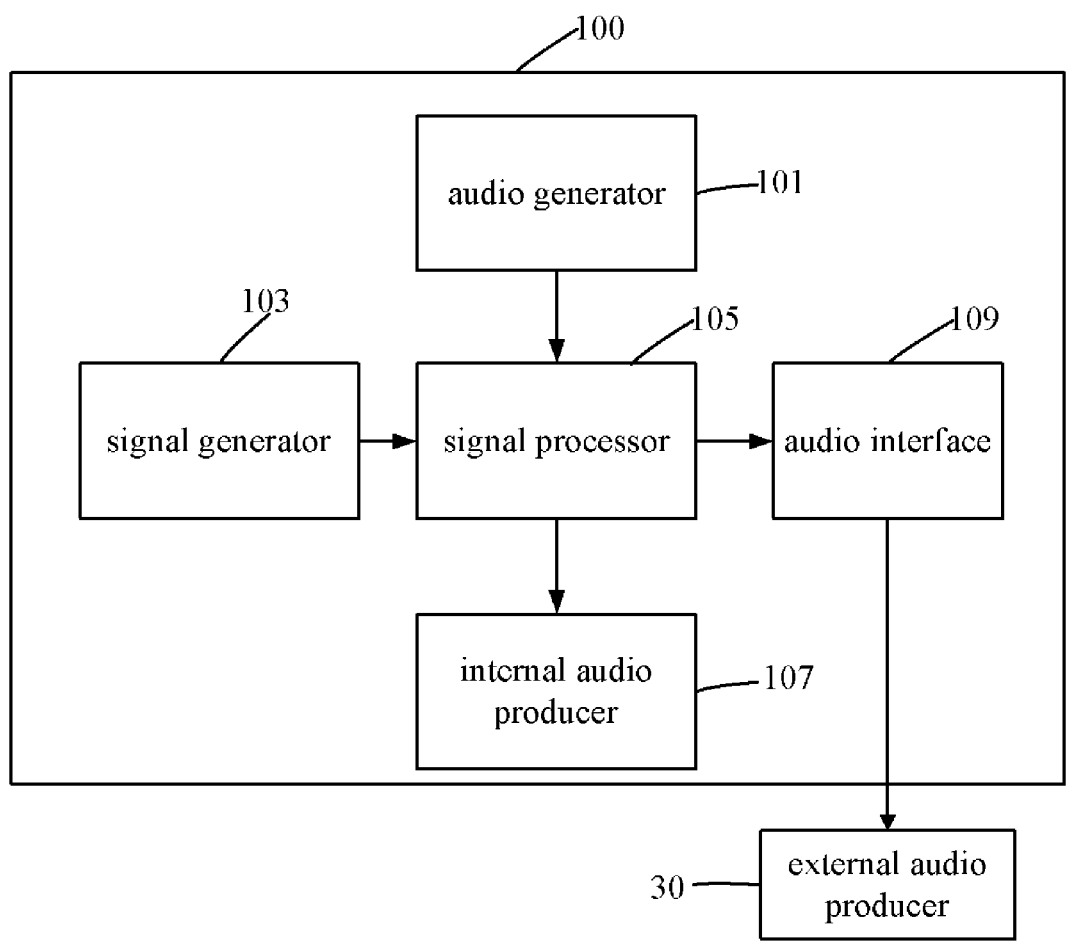
FIG. 1 is a function diagram of a sleep inducing apparatus in accordance with an exemplary embodiment, wherein the sleep inducing apparatus includes a signal processor.

It has been known that when a person is in deep sleep, the person's brain waves slow down to 0.4 hertz (HZ)-4 HZ. A sleep inducing apparatus 100 shown in FIG. 1 is capable of generating/creating acoustic signals mimicking brain wave frequency to assist a person to relax, thereby, inducing to sleep. The sleep inducing apparatus 100 can be applied to persons to treat different conditions, such as treatment of sleep disorders or stress.

Referring to FIG. 1, the sleep inducing apparatus 100 in accordance with an exemplary embodiment includes an audio generator 101, a signal generator 103, a signal processor 105, and an internal audio producer 107. The audio generator 101, the signal generator 103, and the audio producer 107 are electrically connected to the signal processor 105.

The audio generator 101 is configured for generating audio signals. The audio generator 101 may be a decoder for decoding an audio file stored on a media to generate the audio signals. The audio signals may be single tone audio signals which have a same frequency. The signal generator 103 is configured for generating electrical signals with a frequency between 0.4 HZ to 4 HZ. The electrical signals may be square wave signals, and the voltage levels of the electrical signals are changed between the high voltage level and the low voltage level. The signal processor 105 is configured for adjusting amplitudes of the audio signals according to the frequency of the electrical signals that the amplitudes of the audio signals are changed at a frequency between 0.4 HZ and 4 HZ. The internal audio producer 107 may be a speaker for converting the adjusted audio signals into sounds.

The sleep inducing apparatus 100 further includes an audio interface 109 electrically connected to the signal processor 105. The audio interface is used for outputting the adjusted audio signals from the signal processor 105 to an external audio producer 30. The external audio producer 30 may be a speaker or an earphone.

Figure 2:
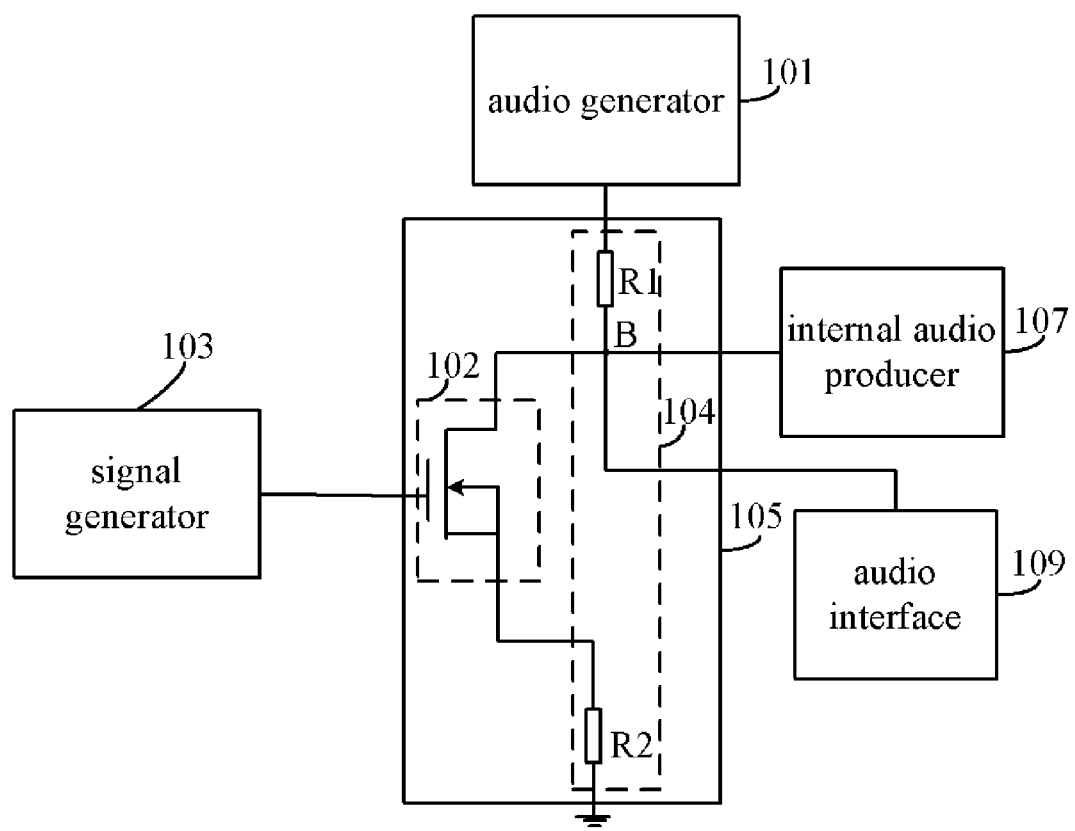
FIG. 2 is a circuit diagram of the signal processor.

Referring to FIG. 2, a circuit diagram of the signal processor 105 is illustrated. The signal processor 105 includes a switch unit 102 and an adjusting unit 104. The switch unit 102 is electrically connected to the signal generator 103. The adjusting unit 104 is electrically connected to the audio generator 101, the switch unit 102, the internal audio producer 107, and the audio interface 109. The switch unit 102 is in an open state when the electrical signals are high, and is in a closed state when the electrical signals are low. The adjusting unit 104 adjusts the amplitudes of the audio signals to a smaller level when the switch unit 102 is in the closed state, and resets the amplitudes of the audio signals when the switch unit 102 is in the open state.

The switch unit 102 may be a metal oxide semiconductor field effect transistor (MOSFET). The adjusting unit 104 may include a first resister R1, and a second resister R2. The gate of the MOSFET is electrically connected to the signal generator 103, the drain of the MOSFET is electrically connected to an output node B, and the source of the MOSFET is grounded via the second resistor R2. One end of the first resistor R1 is electrically connected to the audio generator 101, the other end is electrically connected to the output node B. The output node B is electrically connected to the internal audio producer 107 and the audio interface 109.

Firstly, provided that the electrical signals generated by the signal generator 103 are low, the switch unit 102 is turned off, then the audio signals, with original amplitudes, are sent to the internal audio producer 107 and audio interface 109 directly. For instance, the audio signals' voltage generated by the audio generator 101 is V0, when the switch unit 102 is turned off, the audio signals are transmitted to the first resister R1 but not the second resister R2, thus the voltage of the output node B is equal to V0. In other words, the amplitudes of the audio signals sent to the internal audio producer 107 and the audio interface 109 are the same as the original voltage.

Secondly, provided that the electrical signals generated by the signal generator 103 are high, the switch unit 102 is turned on. The amplitudes of the audio signals are adjusted to a smaller level by the first resistor R1 and the second resistor R2 before the audio signals are sent to the internal audio producer 107 and the audio interface 109. For instance, the audio signals' voltage is V0. When the switch unit 102 is turned on, the audio signals are transmitted to the first resistor R1 and the second resistor R2, thus, the voltage of the output node B is reduced to V0*R2/(R1+R2), and the amplitudes of the audio signals are reduced. In other words, the amplitudes of the audio signals sent to the internal audio producer 107 and the audio interface 109 are lower than the original voltage.

As described above, the voltage level of electrical signals are changeable at a frequency between 0.4 HZ and 4 HZ, the switch unit 102 changes between the closed state and the open state according to this frequency, thus, the amplitudes of the audio signals are adjusted at the frequency between 0.4 HZ and 4 HZ, which is in accordance with the brain wave frequency of deep sleep. In other words, the sleep inducing apparatus 100 may mimic the brain wave frequency to affect people for relaxing, so that people will be induced to sleep.

Figure 3:
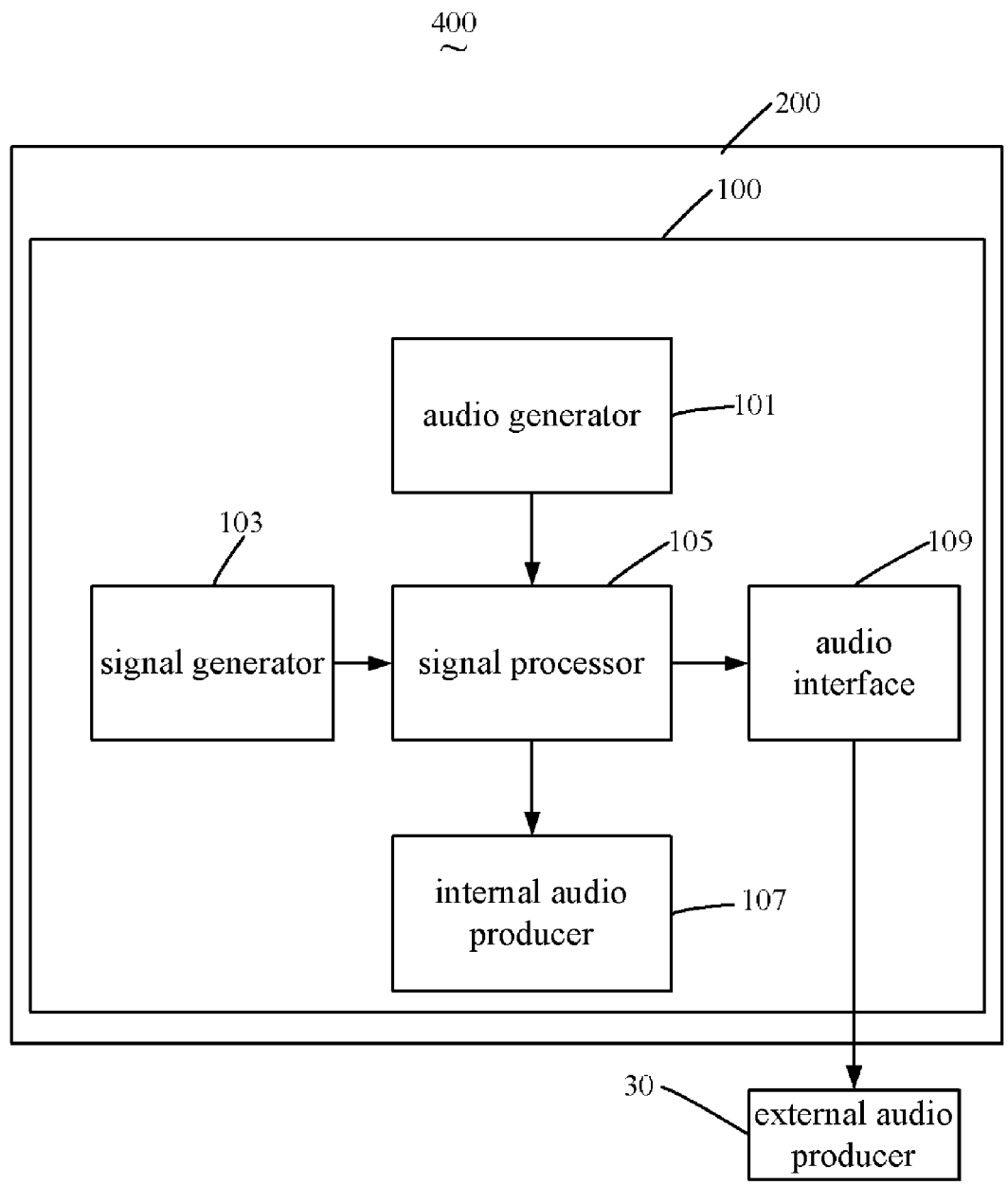
FIG. 3 is a block diagram of an electronic device using the sleep inducing apparatus.

Referring to FIG. 3, the sleep inducing apparatus 100 may be used in an electronic device 400, such as a phone, a PDA, a notebook, and so on. The electronic device 400 includes a main body 200 which may include a housing or a printed circuit board, for securing or disposing the sleep inducing apparatus 100 and other function modules. The internal audio producer 107 and the audio interface 109 of the sleep inducing apparatus 100 may also be a speaker and an audio interface of the electronic device 400. The sleep inducing apparatus 100 generates the audio signals whose amplitudes are changeable at a frequency between 0.4 Hz and 4 HZ, and then transmits the audio signal to the audio producer 107 or the external audio producer 30, detachable connected to the audio interface 109, to construct sounds.

As described above, the electronic device 400 generates the audio signals whose amplitudes are changeable at a frequency between 0.4 HZ and 4 HZ to simulate the brain waves when person in deep sleep. Therefore, the electronic device 400 will relax the body, reduce anxiety and stress, detach awareness, and induce sleep.

It is believed that the present embodiments and their advantages will be understood from the foregoing description, and it will be apparent that various changes may be made thereto without departing from the spirit and scope of the invention or sacrificing all of its material advantages, the examples hereinbefore described merely being preferred or exemplary embodiments of the invention.

What is claimed is:

1. A sleep inducing apparatus comprising:
an audio generator for generating audio signals;
a signal generator for generating electrical signals with a frequency between 0.4 HZ and 4 HZ; and
a signal processor comprising:
a switch unit switching between an open state and a closed state based on the electrical signals, and
an adjusting unit adjusting the amplitudes of the audio signals based on the states of the switch unit;
wherein the switch unit is a metal oxide semiconductor field effect transistor (MOSFET); the adjusting unit comprises a first resistor and a second resistor, and a gate of the MOSFET is electrically connected to the signal generator, a drain is electrically connected to an output node, a source is grounded via the second resistor, one end of the first resistor is electrically connected to the audio generator, the other end is electrically connected to the output node, the output node outputting the adjusted audio signals.

2. The sleep inducing apparatus of claim 1, wherein the electrical signals are square wave signals.

3. The sleep inducing apparatus of claim 1, wherein the audio signals are single tone audio signals.

4. The sleep inducing apparatus of claim 1, further comprising an internal audio producer for converting the adjusted audio signals into sounds.

5. The sleep inducing apparatus of claim 1, further comprising an audio interface for sending the adjusted audio signals to an external audio producer for converting the adjusted audio signals into sounds.

6. The sleep inducing apparatus of claim 1, wherein the switch unit is in the open state when the electrical signals are low, and in the closed state when the electrical signals are high, and the adjusting unit reduces the amplitudes of the audio signals when the switch unit is in closed state.

7. An electronic device comprising:
a sleep inducing apparatus for generating audio signals with periodically variable amplitudes at a frequency between 0.4 HZ and 4 HZ; and
an audio producer electrically connected to the sleep inducing apparatus for converting the adjusting audio signals into sounds;
wherein the sleep inducing apparatus comprises:
an audio generator for generating audio signals;
an adjusting unit; and
a switch unit which can be switched between an open state and a closed state at the frequency to enable the adjusting unit to adjust the amplitudes of the audio signals at the frequency;
wherein the switch unit is a metal oxide semiconductor field effect transistor (MOSFET); the adjusting unit comprises a first resistor and a second resistor, and a gate of the MOSFET is electrically connected to the audio generator, a drain is electrically connected to an output node, a source is grounded via the second resistor, one end of the first resistor is electrically connected to the audio generator, the other end is electrically connected to the output node, the output node outputting the adjusted audio signals.

8. An electronic device comprising:
a main body,
a sleeping inducing apparatus disposed in the main body, wherein the sleeping inducing apparatus comprises:
an audio generator for generating audio signals;
a signal generator for generating electrical signals with a frequency between 0.4 HZ to 4 HZ; and
a signal processor for adjusting amplitudes of the audio signals according to the frequency, and outputting the adjusted audio signals; and
an audio producer for converting the adjusted audio signals into sounds;
wherein the signal processor comprises:
a switch unit being switched from an open state to a closed state at the frequency, an adjusting unit which adjusts the amplitudes of the audio signals based on the states of the switch unit;
wherein the switch unit is a metal oxide semiconductor field effect transistor (MOSFET); the adjusting unit comprises a first resistor and a second resistor, and a gate of the MOSFET is electrically connected to the signal generator, a drain is electrically connected to an output node, a source is grounded via the second resistor, one end of the first resistor is electrically connected to the audio generator, the other end is electrically connected to the output node, the output node outputting the adjusted audio signals.

9. The electronic device of claim 8, wherein the electrical signals are square wave signals.

10. The electronic device of claim 8, wherein the audio signals are single tone audio signals.

* * * * *